United States Patent
Belyaev et al.

(10) Patent No.: US 7,436,505 B2
(45) Date of Patent: Oct. 14, 2008

(54) COMPUTER-IMPLEMENTED METHODS AND SYSTEMS FOR DETERMINING A CONFIGURATION FOR A LIGHT SCATTERING INSPECTION SYSTEM

(75) Inventors: Alexander Belyaev, Mountain View, CA (US); Daniel Kavaldjiev, Milpitas, CA (US); Amith Murali, Fremont, CA (US); Aleksey Petrenko, Milpitas, CA (US); Mike D. Kirk, Los Altos Hills, CA (US); David Shortt, Milpitas, CA (US); Brian L. Haas, San Jose, CA (US); Kurt L. Haller, Pleasanton, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 366 days.

(21) Appl. No.: 11/278,624

(22) Filed: Apr. 4, 2006

(65) Prior Publication Data
US 2007/0229809 A1 Oct. 4, 2007

(51) Int. Cl.
*G01N 21/00* (2006.01)
(52) U.S. Cl. .................................. 356/237.2
(58) Field of Classification Search ... 356/237.1–237.5, 356/601–623, 445–448
See application file for complete search history.

(56) References Cited

U.S. PATENT DOCUMENTS

| | | | |
|---|---|---|---|
| 6,201,601 B1 | 3/2001 | Vaez-Iravani et al. | |
| 6,271,916 B1 | 8/2001 | Marxer et al. | |
| 6,538,730 B2 | 3/2003 | Vaez-Iravani et al. | |
| 6,943,941 B2 | 9/2005 | Flagello et al. | |
| 6,950,196 B2 | 9/2005 | Fielden et al. | |
| 7,221,501 B2 | 5/2007 | Flagello et al. | |
| 7,286,218 B2 * | 10/2007 | Tiemeyer et al. | 356/237.2 |
| 2007/0252977 A1 * | 11/2007 | Baran et al. | 356/239.7 |

OTHER PUBLICATIONS

Stokowski, "The Physics of our Enterprise," presented Mar. 11, 1998, 83 pages.

* cited by examiner

*Primary Examiner*—Hoa Q Pham
(74) *Attorney, Agent, or Firm*—Baker & McKenzie LLP

(57) ABSTRACT

Computer-implemented methods and systems for determining a configuration for a light scattering inspection system are provided. One computer-implemented method includes determining a three-dimensional map of signal-to-noise ratio values for data that would be acquired for a specimen and a potential defect on the specimen by the light scattering inspection system across a scattering hemisphere of the inspection system. The method also includes determining one or more portions of the scattering hemisphere in which the signal-to-noise ratio values are higher than in other portions of the scattering hemisphere based on the three-dimensional map. In addition, the method includes determining a configuration for a detection subsystem of the inspection system based on the one or more portions of the scattering hemisphere.

22 Claims, 5 Drawing Sheets

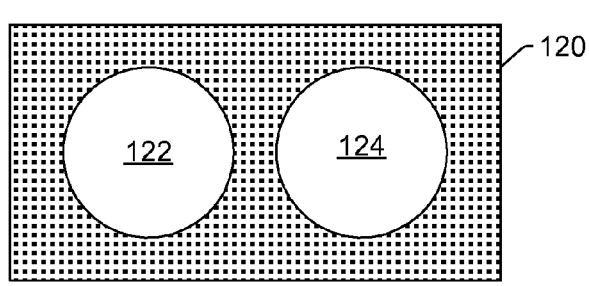
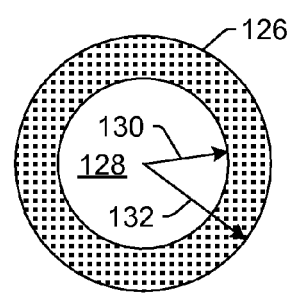
Fig. 6
Fig. 7
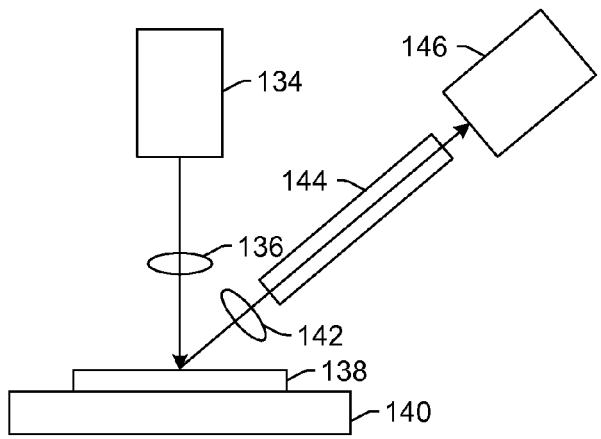
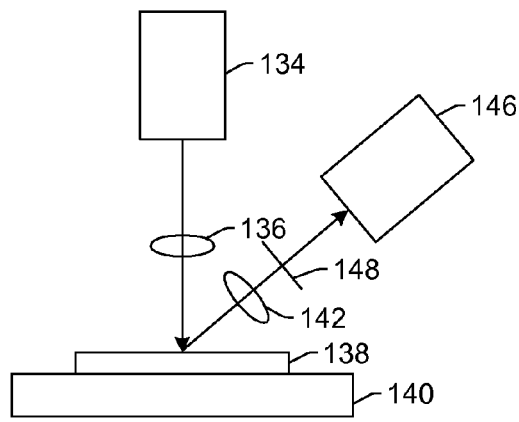
Fig. 8
Fig. 9
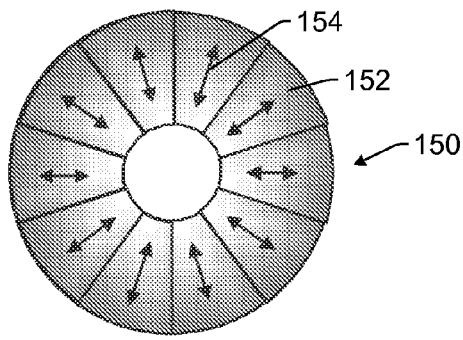
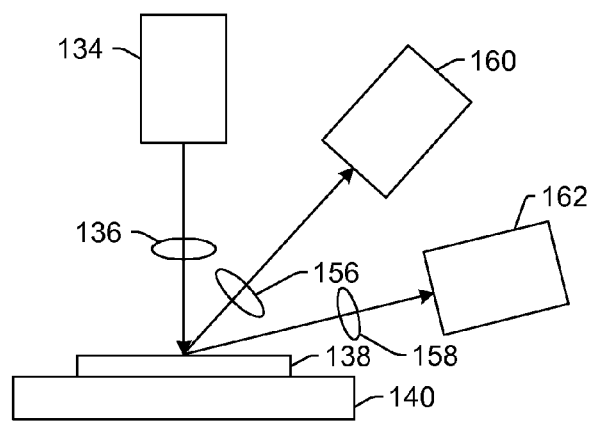
Fig. 10
Fig. 11

COMPUTER-IMPLEMENTED METHODS AND SYSTEMS FOR DETERMINING A CONFIGURATION FOR A LIGHT SCATTERING INSPECTION SYSTEM

BACKGROUND OF THE INVENTION

1. Field of the Invention

The present invention generally relates to computer-implemented methods and systems for determining a configuration for a light scattering inspection system. Certain embodiments relate to determining a configuration for a detection subsystem of a light scattering inspection system based on a three-dimensional map of signal-to-noise ratio values for data that would be acquired for a specimen and a potential defect on the specimen by the inspection system.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various times during a semiconductor manufacturing process to detect defects on wafers. Inspection has always been an important part of fabricating semiconductor devices such as integrated circuits. However, as the dimensions of semiconductor devices decrease, inspection becomes even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Often, increased defect detection sensitivity can be achieved by system configurations that result in reduced throughput. For example, the sensitivity of currently available inspection systems can be increased by reducing the size of the spot on the wafer that is illuminated during inspection. The size of the illuminated spot on the wafer may be reduced relatively simply in many currently used inspection systems (e.g., by altering or adding an optical element to the beam forming optics train). Reducing the spot size effectively decreases the amount of light that is scattered from the surface of the wafer relative to the defect scattering, thereby increasing the defect signal-to-noise ratio and the sensitivity of the system. However, reducing the spot size also reduces the throughput of the system since scanning a smaller size spot over an entire wafer surface takes longer than scanning a larger size spot over the wafer surface. Therefore, by varying the spot size, it is possible to trade-off throughput for sensitivity.

Other changes can also or alternatively be made to currently available inspection systems to increase the sensitivity of the inspection systems. For example, the collector of some currently available inspection systems may be altered by changing or adding an aperture to the collector. The aperture may be configured to block light that is scattered from the surface of the wafer while allowing light scattered from a defect to pass through the aperture thereby increasing the defect signal-to-noise ratio and the sensitivity of the system. In another example, the light source of currently available inspection systems may be replaced with a higher power light source. For example, if an inspection system is configured for a laser power of about 350 mW, the laser power of the system can be increased to about 1000 mW. Increasing the power of the light source generally increases the level of light scattered from defects thereby increasing the sensitivity of the system.

To increase the sensitivity of the inspection system, the configuration of the detector of the inspection system may also or alternatively be altered. In particular, in the field of semiconductor wafer inspection with scanning laser light scattering inspection systems, the concept of an optimal detector, one that maximizes the ratio of captured light from defects of interest on the surface to background noise arising from diffuse reflectance of the laser spot on that surface, is known to practitioners of the art. For example, S. Stokowski, "The Physics of Our Enterprise," a presentation given on Mar. 11, 1998, which is incorporated by reference as if fully set forth herein, outlined the process of modeling defect scattering as well as background surface scattering from the power spectral density (PSD) function and included the concept of the optimal detector for 60 nm polystyrene latex (PSL) spheres on bare silicon.

However, heretofore, determining a truly optimized detector required experimental measurements of the spatial distribution of scattered light from a defect and the diffuse scattering pattern from a physical specimen. Based on such data, a configuration can be determined for arrays of optical detectors and/or an aperture in the scattered light collection optics train of any single detector and/or parameters of a variable aperture in the collection optics train (realized, for example, by mechanical baffles and/or liquid crystal display (LCD)-based electronically controlled light values) such that the defect signal to background surface noise ratio is maximized.

Besides the time consuming and error prone experimental measurements that are performed with expensive laboratory equipment unsuited to the semiconductor fab environment, the methods described above are also disadvantageous for end users of the inspection systems who have to select representative wafers and ship them to a remote location (e.g., usually to the facilities of the inspection system manufacturer) for these measurements. Therefore, development cycles for different types of substrates are unacceptably long, and real time optimization of the detector in the fab of the end user is out of the question.

Accordingly, it would be advantageous to develop methods and systems for determining a configuration for a light scattering inspection system without performing measurements of a wafer with the inspection system thereby reducing error in the determined configuration, reducing the time in which the configuration is determined, and increasing the accuracy of the configuration.

SUMMARY OF THE INVENTION

The following description of various embodiments of computer-implemented methods and systems is not to be construed in any way as limiting the subject matter of the appended claims.

One embodiment relates to a computer-implemented method for determining a configuration for a light scattering inspection system. The method includes determining a three-dimensional (3D) map of signal-to-noise ratio (S/N) values for data that would be acquired for a specimen and a potential defect on the specimen by the light scattering inspection system across a scattering hemisphere of the inspection system. The method also includes determining one or more portions of the scattering hemisphere in which the S/N values are higher than in other portions of the scattering hemisphere based on the 3D map. In addition, the method includes determining a configuration for a detection subsystem of the inspection system based on the one or more portions of the scattering hemisphere.

In one embodiment, the scattering hemisphere includes an entire scattering hemisphere of the inspection system. In another embodiment, determining the 3D map includes determining different 3D distributions of light that would be diffusely reflected from the specimen and the potential defect when illuminated by the inspection system and determining the 3D map from the different 3D distributions.

In an additional embodiment, determining the 3D map includes determining a 3D distribution of light that would be diffusely reflected from the specimen when illuminated by the inspection system based on a power spectral density (PSD) function determined from metrology data for the specimen. In a further embodiment, determining the 3D map includes determining a 3D distribution of light that would be diffusely reflected from the specimen when illuminated by the inspection system based on a PSD function determined from metrology data for the specimen and information about one or more films that will be present on the specimen and are at least partially transparent to illumination by the inspection system. In some embodiments, determining the 3D map includes determining a 3D distribution of light that would be diffusely reflected from the potential defect based on optical constants of the potential defect and complex indices of the specimen.

In one embodiment, prior to determining the one or more portions of the scattering hemisphere, the method includes removing one or more portions of the 3D map based on areas of the scattering hemisphere in which the inspection system cannot collect light. In some embodiments, the configuration includes positions of one or more detectors in the scattering hemisphere. In another embodiment, the detection subsystem includes more than one detector configured to generate signals during inspection of the specimen. In one such embodiment, the configuration includes the signals generated by which of the more than one detector that will be used for detection of the potential defect.

In some embodiments, the configuration includes one or more parameters of an aperture plate positioned in the scattering hemisphere. In one such embodiment, the aperture plate includes one or more fixed openings. In a different such embodiment, the aperture plate includes one or more adjustable openings. In another embodiment, the configuration includes one or more parameters of a baffle positioned in the scattering hemisphere.

In some embodiments, the configuration includes one or more parameters of a linear polarizing filter positioned in the scattering hemisphere. In one such embodiment, the linear polarizing filter includes a plurality of linear polarizing segments. In another embodiment, the configuration includes one or more parameters of an electro-optical light filter positioned in the scattering hemisphere.

In one embodiment, the method includes providing signals to a control subsystem of the inspection system that are responsive to the configuration and can be used by the control subsystem to cause the detection subsystem to have the determined configuration. In another embodiment, the method includes determining a configuration for an additional detection subsystem of the inspection system based on other portions of the scattering hemisphere such that the additional detection subsystem in the determined configuration is sensitive to changes in the specimen and is not sensitive to the potential defect. In a further embodiment, the method is performed for the specimen and a different potential defect to determine an additional configuration for the detection subsystem. In one such embodiment, data acquired by the inspection system during different scans of the specimen with the configuration and the additional configuration can be used to classify defects detected in the data. Each of the embodiments of the method described above may include any other step(s) of any other method(s) described herein.

Another embodiment relates to a system configured to determine a configuration for a light scattering inspection system. The system includes a simulation engine configured to determine a 3D map of S/N values of data that would be acquired for a specimen and a potential defect on the specimen by the light scattering inspection system across a scattering hemisphere of the inspection system. The system also includes a processor configured to determine one or more portions of the scattering hemisphere in which the S/N values are higher than in other portions of the scattering hemisphere based on the 3D map. The processor is also configured to determine a configuration for a detection subsystem of the inspection system based on the one or more portions of the scattering hemisphere. The system may be further configured as described herein.

An additional embodiment relates to a system configured to determine an inspection system configuration for a specimen. The system includes a light scattering inspection system that includes a control subsystem configured to alter one or more parameters of a detection subsystem of the inspection system. The system also includes a simulation engine configured to determine a 3D map of S/N values of data that would be acquired for the specimen and a potential defect on the specimen by the inspection system across a scattering hemisphere of the inspection system. In addition, the system includes a processor configured to determine one or more portions of the scattering hemisphere in which the S/N values are higher than in other portions of the scattering hemisphere based on the 3D map, to determine a configuration for the detection subsystem based on the one or more portions of the scattering hemisphere, and to provide signals to the control subsystem that are responsive to the configuration and can be used by the control subsystem to cause the detection subsystem to have the determined configuration.

In one embodiment, the simulation engine is configured to determine the 3D map based on information about the specimen acquired by a metrology system. In another embodiment, the simulation engine is configured to determine the 3D map for different specimens based on information about the different specimens. In one such embodiment, the processor is configured to determine the configuration for the detection subsystem for the different specimens and to provide different signals to the control subsystem of the inspection system in real time based on the specimen being inspected by the inspection system. The different signals are responsive to the configurations and can be used by the control subsystem to cause the detection subsystem to have one of the determined configurations. Each of the embodiments of the system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIGS. 6-7 are schematic diagrams illustrating a cross-sectional view of various embodiments of an aperture plate, one or more parameters of which may be included in a configuration determined according to embodiments described herein;

FIGS. 8-9 are schematic diagrams illustrating a side view of light scattering inspection systems that include a detection subsystem for which a configuration may be determined according to embodiments described herein;

FIG. 10 is a schematic diagram illustrating a cross-sectional view of a linear polarizing filter that includes a plurality of linear polarizing segments and that may be positioned in a scattering hemisphere of a light scattering inspection system;

FIGS. 11-12 are schematic diagrams illustrating a side view of light scattering inspection systems that include one or more detection subsystems for which configurations may be determined according to embodiments described herein;

Figure 1:
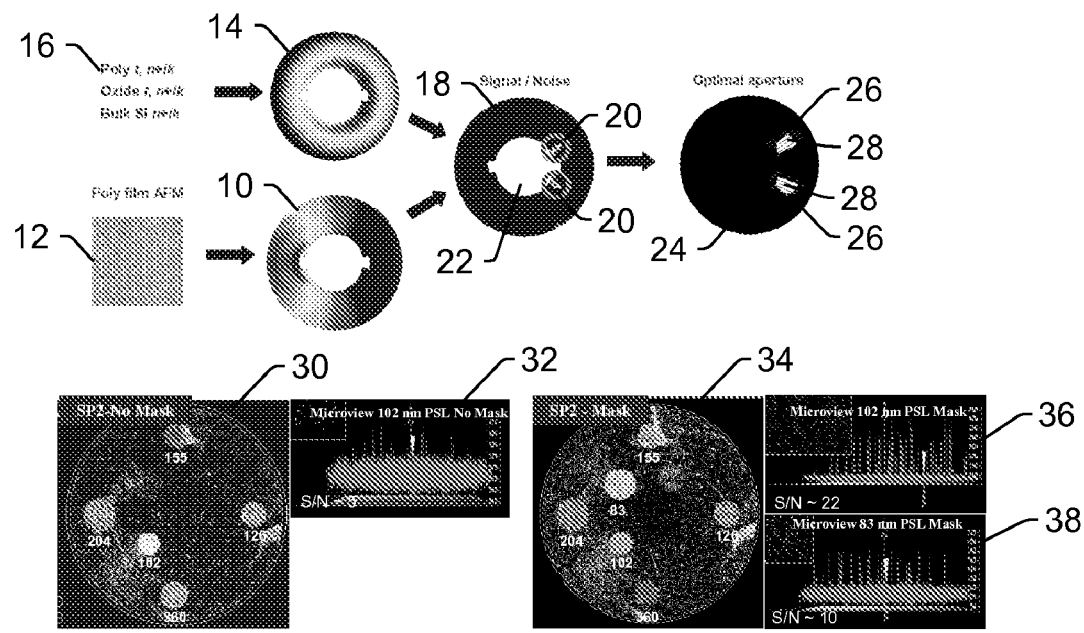
FIG. 1 includes simulated data illustrating one embodiment of a computer-implemented method for determining a configuration for a light scattering inspection system and results acquired using an initial configuration for the inspection system and a configuration for the inspection system determined according to embodiments described herein.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESRIPTION OF THE PREFERRED EMBODIMENTS

As used herein, the term "specimen" generally refers to a wafer. However, although embodiments are described herein with respect to a wafer, it is to be understood that the embodiments described herein may used to determine a configuration for a light scattering inspection system used for any other specimen, and in particular any specimen for which increased defect detection sensitivity is desirable.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for determining a configuration for a light scattering inspection system. The method includes determining a three-dimensional (3D) map of signal-to-noise ratio (S/N) values for data that would be acquired for a specimen and a potential defect on the specimen by the light scattering inspection system across a scattering hemisphere of the inspection system. In one embodiment, the scattering hemisphere includes an entire scattering hemisphere of the inspection system.

In some embodiments, determining the 3D map includes determining different 3D distributions of light that would be diffusely reflected from the specimen and the potential defect when illuminated by the inspection system and determining the 3D map from the different 3D distributions. One example of such 3D distributions of light are shown in FIG. 1. For example, one embodiment of the computer-implemented method includes determining 3D distribution of light 10 that would be diffusely reflected from a specimen (not shown). 3D distribution of light 10 may be determined using, for example, a surface scatter model. 3D distribution of light 10 is a false color light scattering intensity map that depicts the "detector's eye view" of the wide channel collector of the inspection system (not shown in FIG. 1) described in more detail with reference to FIG. 12. However, it is to be understood that the embodiments described herein can be performed for any inspection system described herein or any other inspection system known in the art.

The specimen is, in this example, a silicon wafer on which a silicon dioxide layer is formed. A polysilicon layer is formed on the silicon dioxide layer. In one example, the polysilicon layer has a thickness of about 800 Å and is relatively rough. Determining a configuration of a light scattering inspection system for such a specimen is particularly advantageous since the background light scattering ("haze") from the grain structure of polysilicon films is known to reduce the achievable sensitivity of unpatterned wafer inspection systems.

In one embodiment, determining the 3D map includes determining 3D distribution of light 10 that would be diffusely reflected from the specimen when illuminated by the inspection system based on a power spectral density (PSD) function determined from metrology data 12 for the specimen. In this manner, the 3D distribution (over the full solid angle of the scattering hemisphere of the inspection system)

of the diffusely reflected light from the specimen may be determined using the PSD as input. The metrology data may be, for example, data acquired for the specimen using an atomic force microscope (AFM) or any other suitable metrology system known in the art. The data may be data responsive to roughness of the specimen. The PSD function may be determined from the metrology data using any method and/or algorithm known in the art.

In another embodiment, determining the 3D map includes determining a 3D distribution of light that would be diffusely reflected from the specimen when illuminated by the inspection system based on a PSD function determined from metrology data for the specimen and information about one or more films that will be present on the specimen and are at least partially transparent to illumination by the inspection system. In this manner, if a thin film or stack of films that is semi-transparent or transparent at the wavelength(s) of the inspection system are formed on the specimen, the method takes into account the thickness(es) and complex refractive index (indices) of the film(s).

This embodiment of the computer-implemented method also includes determining 3D distribution of light 14 that would be diffusely reflected from a potential defect on the specimen. 3D distribution of light 14 is a false color light scattering intensity map that depicts the same "detector's eye view" described above. In one example, the potential defect is a polystyrene latex (PSL) sphere. In this example, 3D distribution of light 14 may be determined using a PSL sphere scattering model. In one embodiment, determining the 3D map includes determining a 3D distribution of light that would be diffusely reflected from the potential defect based on optical constants of the potential defect and complex indices of the specimen. For example, for the specimen described above, 3D distribution of light 14 that would be diffusely reflected from the potential defect can be determined based on optical constants of the PSL sphere and complex indices 16 of the specimen that include complex indices (n and k) and thicknesses of bulk silicon, silicon dioxide, and polysilicon. The method can also be performed for defects, such as but not limited to, spherical and non-spherical particles, using optical constants of materials that commonly particulate and deposit on wafers during the semiconductor fabrication process and the complex indices of the substrate and thin film thicknesses (if any). Modeled defects may further include, without limitation, scratches and pits in the substrate surface, thin stains from imperfect drying after wet clean and other wet chemical wafer processing.

In this manner, the embodiments described herein take advantage of advances in highly accurate modeling of light scattering from defects on diffusely reflective surfaces to determine a configuration for a detection subsystem of an inspection system (e.g., optimized detectors) without requiring a physical specimen of a given substrate type. The only experimental data used in embodiments described herein may be the surface roughness of a particular substrate type, the thickness of one or more thin films if formed on the substrate, and experimental or known values of the complex refractive indices of the substrate and thin film materials. In addition, the embodiments described herein take advantage of known and established metrology techniques. For example, surface roughness is easily and often routinely measured during normal wafer fab operations with commercially available AFM systems known in the art. Thin film thicknesses and complex indices of refraction are also routinely measured in the fab with substantially high accuracy using commercially available spectroscopic reflectometry and/or spectroscopic ellipsometry systems known in the art. Examples of systems that may be used to perform the measurements described herein are illustrated in U.S. Pat. No. 6,950,196 to Fielden et al., which is incorporated by reference as if fully set forth herein.

3D distributions of light 10 and 14 may be used to determine 3D map 18 of S/N values for data that would be acquired for the specimen and the potential defect on the specimen by the light scattering inspection system across a scattering hemisphere of the inspection system. For example, 3D map 18 may be determined by dividing 3D distribution 14 by the noise implied by 3D distribution 10.

The method also includes determining one or more portions of the scattering hemisphere in which the S/N values are higher than in other portions of the scattering hemisphere based on the 3D map. In one such example, in 3D map 18 shown in FIG. 1, the S/N values of portions 20 of the 3D map are determined to be higher than in other portions of the 3D map. In particular, portions 20 of the 3D map have the highest S/N values in the map. Therefore, portions 20 may be used to determine the corresponding portions of the scattering hemisphere in which the S/N values will be higher than in other portions of the scattering hemisphere. Although two portions 20 are shown in FIG. 1, it is to be understood that the method may determine that any number of portions (e.g., one, two, three, etc.) of the scattering hemisphere have S/N values that are higher than other portions of the scattering hemisphere. The portion(s) of the scattering hemisphere having the higher S/N values may be located at any position(s) in the scattering hemisphere.

In some embodiments, the 3D map of the S/N values may be considered as the S/N of a hypothetical detector configured to collect light from the complete 3D scattering hemisphere of the inspection system. In this manner, the method may include determining by iterative search and/or other optimization techniques which portions of the hemisphere, if not collected, increase the S/N of the detector relative to the full-hemisphere S/N of the detector. The remaining portion(s) of the scattering hemisphere may then be used to determine the configuration of the inspection system as described further herein. Such a S/N map has not previously been used in such a manner.

As described above, the scattering hemisphere may include an entire scattering hemisphere of the inspection system. In some embodiments, prior to determining the one or more portions of the scattering hemisphere, the method includes removing one or more portions of the 3D map based on areas of the scattering hemisphere in which the inspection system cannot collect light. For example, in a light scattering inspection system, the opto-mechanical configuration of the inspection system usually limits light collection to less than $2\pi$ (i.e., the solid angle subtended by a hemisphere) in units of steradian (sr)). Therefore, the optimization described above may be constrained by setting as "uncollectible" those portions of the scattering hemisphere corresponding to the limited collection space of the inspection system. In addition, the optimization may begin with the full hemisphere across which light can be collected by the fixed collector(s) of a particular inspection system. The optimization may then be performed to determine restrictions on this full hemisphere that can be made with elements such as field stops, masks, light valves, etc. to increase the sensitivity of the system. In this manner, the optimization may eliminate a portion or portions of the full scattering hemisphere of an inspection system depending on how the S/N can be optimized for a particular specimen.

In one such example, as shown in FIG. 1, portion 22 of 3D map 18 corresponds to areas of the scattering hemisphere in which the inspection system cannot collect light. The central region of portion 22 of 3D map 18 may correspond to a spatial filter (not shown) of the inspection system that is used to block normal illumination specularly reflected from the specimen and therefore also blocks collection of scattered light in this portion of the scattering hemisphere. The regions of portion 22 extending from the central region may correspond to mechanical components, the position of which prevents light collection in these regions of the scattering hemisphere of the inspection system.

The method also includes determining a configuration for a detection subsystem of the inspection system based on the one or more portions of the scattering hemisphere. For example, as shown in FIG. 1, configuration 24 may be determined based on portions of the scattering hemisphere that correspond to portions 20 of the 3D map. Configuration 24 includes one or more parameters of apertures 26. The parameter(s) of apertures may include, for example, positions of the apertures in the scattering hemisphere, positions of the openings in the apertures, one or more dimensions of the openings, and shape of the openings. In the example shown in FIG. 1, the parameter(s) of apertures 26 may be determined such that the positions of the openings in the apertures correspond to the positions of portions 20 in the 3D map. In this configuration, the detection subsystem may not detect light scattered in portions of the scattering hemisphere other than those corresponding to the openings of the apertures. In other words, the determined optimal configuration realized in practice may be an aperture plate that contains one or more openings that allow scattered light to pass from the specimen to the detector(s) of the inspection system. In this manner, the embodiments described herein can be used to determine an optimal configuration for an aperture plate positioned in the scattering hemisphere of the inspection system for a particular specimen using only nominal film thickness, refractive indices, and metrology data for the specimen as inputs.

The optimal configuration determined above may be further refined by determining the effect that polarizing filter element(s) placed in the path(s) of the detected light will have on the sensitivity of the inspection system. In this manner, in some embodiments, the configuration also includes parameter(s) of one or more linear polarizing filters positioned in the scattering hemisphere. For example, configuration 24 includes one or more parameters of linear polarizing filters 28 disposed in the openings of apertures 26. In this manner, the determined optimal configuration may be realized by positioning linear polarizing filters in the opening(s) of an aperture plate. In some embodiments, the polarizing filter includes a plurality of segments, each of which is a linear polarizing filter arranged azimuthally in the aperture plate openings. Such an embodiment of a polarizing filter (which may be commonly referred to as a "pizza-pie" polarizer) is described further herein. The linear polarizing filters may also be disposed in any location with respect to the openings such that light that passes through the openings also passes through the linear polarizing filters. In other words, the linear polarizing filters do not have to be disposed in the openings, but may be disposed upstream or downstream of the aperture.

As described above, configuration 24 is determined based on the portions of the scattering hemisphere that have higher S/Ns than other portions of the scattering hemisphere. Therefore, the method may be used to determine the optimal inspection system configuration for specimens that include rough films and other specimens described herein. In addition, the method may be used to determine the optimal configuration using a S/N value model and a 3D distribution of light that would be diffusely reflected from the specimen based on AFM data or other metrology data without sample wafers being measured on the light scattering inspection system.

FIG. 1 also illustrates results obtained using a light scattering inspection system in an initial configuration and in a configuration determined according to embodiments described herein. All of the experimental results described herein are not limiting embodiments of the present invention. The results were obtained by inspecting the same wafer with the different configurations. PSL spheres having different sizes were deposited on the wafer prior to inspection. Results 30 were acquired using the SP2 system that is commercially available from KLA-Tencor, San Jose, Calif. In the initial configuration of the SP2 system used to acquire results 30, no aperture plate or mask was positioned in the scattering hemisphere of the system. The numbers shown in results 30 indicate the size of the PSL spheres detected on the wafer. These results indicate that PSL spheres having diameters of 360 nm, 204 nm, 155 nm, 126 nm, and 102 nm were detected, and 83 nm diameter PSL spheres were not detected. Results 32 corresponding to results 30 indicate that the S/N with which the 102 nm PSL spheres were detected on the wafer was about 5. Therefore, the S/N of this configuration of the SP2 system is not sufficient for detection of the 102 nm PSL spheres with relatively good sensitivity. As such, the smallest PSL sphere size that can be detected by the SP2 system in the initial configuration is 126 nm.

Results 34 were acquired using the same SP2 system. However, the configuration of the SP2 system that was used to acquire results 34 included the aperture plate or mask determined as described above and shown in configuration 24. As shown in results 34, in this configuration, the system detected PSL spheres having diameters of 360 nm, 204 nm, 155 nm, 126 nm, 102 nm, and 83 nm. In addition, results 36 corresponding to results 34 indicate that the S/N with which the 102 nm PSL spheres were detected on the wafer was about 22. Results 38 corresponding to results 34 indicate that the S/N with which the 83 nm PSL spheres were detected on the wafer was about 10. Therefore, the configuration of the inspection system determined according to embodiments described herein can be used to detect defects having sizes as small as 83 nm. In this manner, the SP2 system having the configuration determined according to embodiments described herein has at least a 34% improvement in the detectability of PSL spheres compared to the SP2 system having the original configuration.

Using a detection subsystem configuration determined as described herein can produce such dramatic improvements in defect detection capability because larger defects tend to scatter light with a different distribution than smaller defects. In particular, larger defects tend to scatter light asymmetrically. As defect size decreases, the light scatter distribution from the defects tends to become more symmetrical. Therefore, a mask designed for optimal detection of relatively large defects with asymmetric scattering distributions may not be optimal for relatively small defects with relatively symmetric scattering distributions. As such, the embodiments described herein can be used to provide an optimal configuration for a particular defect type having a particular size. In this manner, the embodiments described herein can be used to determine if and what modifications to existing inspection systems can be made to extend the sensitivity of the inspection systems for smaller defect sizes.

The embodiments described herein have a number of advantages over other methods and systems for determining a configuration for an inspection system. For example, as described further above, the embodiments described herein can be used to determine the optimal configuration for an inspection system using input solely from external metrologies such as roughness from AFM, substrate material complex indices, and film thicknesses and complex indices, if present, on the specimen of interest. In this manner, end users of the inspection system do not have to provide physical specimens of the substrate types to the system manufacturer to determine optimal detectors for each substrate type. In addition, inspection system manufacturers do not need to perform time-consuming, error-prone experimental measurements on the physical specimens. Another advantage is that the possibility of determining the inspection system configuration using experimental results for a relatively small sample of specimens that is unrepresentative of the specimen type is reduced since the end user can provide the system manufacturer with AFM and thickness data from multiple wafers over time. Such data can be used to determine an "average" PSD for the specimen type that can be used to determine a "nearly-optimal" configuration that will be robust to normal process variations.

Furthermore, as described further herein, the determined configuration can be used to drive computer-controlled devices to create the optimal configuration in the inspection system. As such, roughness and thickness data can be fed-forward in real time to assure that the optimal configuration is used on an individual wafer basis. Moreover, by using the 3D maps described herein, the iterative optimization can be started from a "reasonable guess" of the optimized configuration, thereby assuring better convergence of the optimization (e.g., the optimization algorithm) in a reasonable amount of time.

Figure 2:
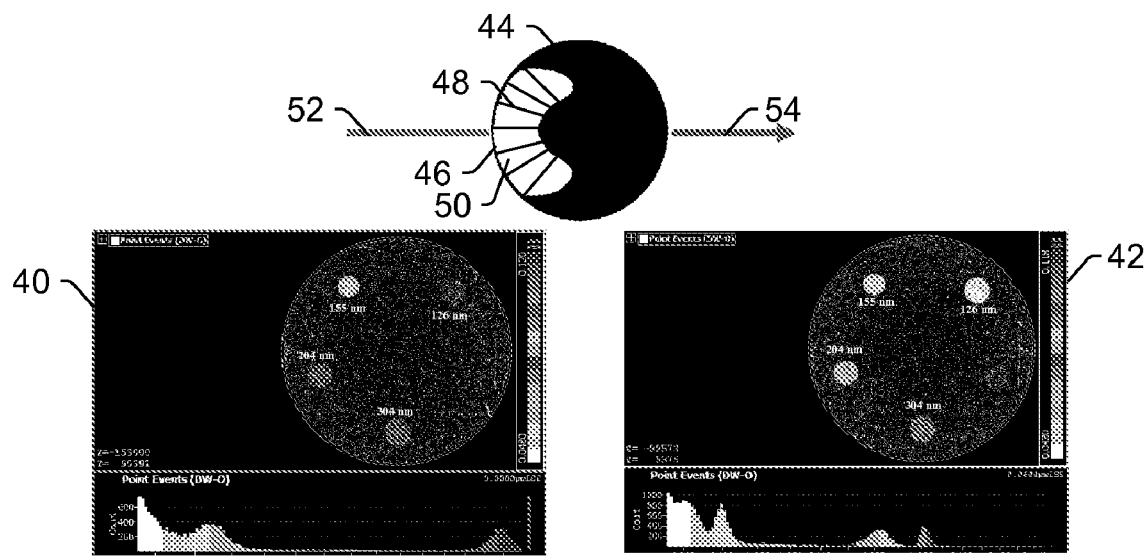
FIG. 2 includes results acquired using an initial configuration for a light scattering inspection system and a configuration for the inspection system determined according to embodiments described herein.

FIG. 2 illustrates results obtained for a different specimen using a light scattering inspection system in an initial configuration and in a configuration determined according to embodiments described herein. In this instance, the specimen was a wafer on which a copper film was deposited by electrochemical deposition (ECD). In this manner, the embodiments described herein may be used to determine the optimal inspection system configuration for a copper film. The results were obtained by inspecting the same wafer with the different configurations. PSL spheres having different sizes were deposited on the wafer prior to inspection. Results 40 were acquired using the SP2 system. In the initial configuration of the SP2 system used to acquire results 40, no aperture plate or mask was positioned in the scattering hemisphere of the system. The numbers shown in results 40 indicate the size of the PSL spheres detected on the wafer. These results indicate that PSL spheres having diameters of 304 nm, 204 nm, and 155 nm and, 126 nm diameter PSL spheres were not detected. As such, the smallest PSL sphere size that can be detected by the SP2 system in this configuration is 155 nm.

Results 42 were acquired using the same SP2 system. However, configuration 44 of the SP2 system that was used to acquire results 42 was determined according to embodiments described herein and included an aperture plate or mask having opening 46 and linear polarizer 48 that includes a plurality of linear polarizing segments 50. Such a linear polarizer may be commonly referred to as a "pizza pie" polarizer due to the arrangement of the linear polarizing segments. Illumination beam 52 was used for this configuration. Beam 54 is the light specularly reflected from the wafer.

As shown in results 42, this configuration of the system detected PSL spheres having diameters of 304 nm, 204 nm, 155 nm, and 126 nm. Therefore, the inspection system in the configuration determined according to embodiments described herein can be used to detect defects having sizes as small as 126 nm. In this manner, the SP2 system having the configuration determined according to embodiments described herein has at least a 19% improvement in the detectability of the PSL spheres compared to the SP2 system having the original configuration. As such, the experimental results illustrate a significant improvement in PSL sphere detection sensitivity using a configuration determined according to embodiments described herein. Therefore, configuration 44 may be the optimal inspection system configuration for inspection of wafers on which a copper film has been electrochemically deposited.

As described above, the method embodiments described herein include determining a configuration for a detection subsystem of an inspection system, and the configuration may include parameters of an aperture or mask and parameters of one or more polarizers. The configuration of the detection subsystem that is determined by the embodiments described herein may also or alternatively include other parameter(s) of the detection subsystem. All of the different parameters of the detection subsystem that are described herein may be included in a determined configuration in any combination.

Figure 3:
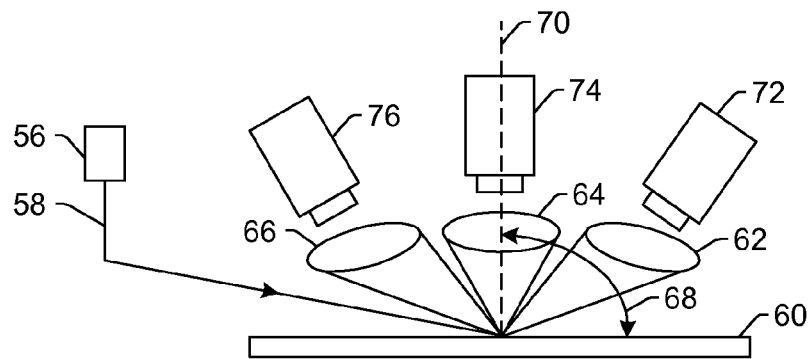
FIGS. 3-5 are schematic diagrams illustrating a side view, a top view, and a perspective view, respectively, of light scattering inspection systems that include a detection subsystem for which a configuration may be determined according to embodiments described herein.

In one embodiment, the configuration determined by the embodiments described herein includes positions of one or more detectors in the scattering hemisphere. The positions of the detector(s) may be defined in any manner known in the art (e.g., by azimuthal, polar, elevation angles, or some combination thereof). One embodiment of a light scattering inspection system for which a configuration may be determined according to embodiments described herein is shown in FIG. 3.

In this embodiment, the inspection system includes light source 56. Light source 56 may include any suitable light source known in the art. Light source 56 may be coupled to one or more optical components (not shown) such that the combination of the light source and the optical component(s) directs light 58 to specimen 60 at an oblique angle of incidence. The optical component(s) may include any suitable optical components known in the art such as reflecting mirrors, acousto-optical deflectors (AODs), etc. Light 58 may be directed to specimen 60 at any suitable oblique angle of incidence.

The inspection system also includes a detection subsystem. The detection subsystem includes collectors 62, 64, and 66. Collectors 62, 64, and 66 may be refractive optical elements. In alternative embodiments, each of the collectors may include one or more refractive optical elements and/or one or more reflective optical elements. Each of the collectors is configured to collect light scattered from the specimen over the same range of azimuthal angles and a different range of polar angles. As used herein, the term "polar angle" is defined as the angle (e.g., angle 68) at which light is scattered from the specimen as measured from normal 70 to the surface of the specimen. As used herein, the term "azimuthal angle" is defined as the angle at which light is scattered from the specimen as measured from the plane of incidence. Therefore, collectors 62, 64, and 66 collect light scattered from the specimen across different two-dimensional (2D) spaces within the scattering hemisphere.

As described above, the collectors collect light scattered at the same range of azimuthal angles but different ranges of polar angles. For example, the collectors may be arranged such that the axis of each collector is centered in the plane of incidence. In this manner, the collection optics of the inspection system may be symmetrical about the plane of incidence. As such, the collectors may be configured in an azimuthal symmetric optical arrangement. In addition, although the axis of collector 64 is shown centered on normal in FIG. 3, the position of the axis of this collector may be offset from normal depending on, for instance, characteristics of the specimen or the defects of interest.

The detection subsystem also includes detectors 72, 74, and 76, which are configured to detect the light collected by collectors 62, 64, and 66, respectively. Detectors 72, 74, and 76 may include any suitable detectors known in the art. Detectors 72, 74, and 76 are configured to generate output signals responsive to the light collected by collectors 62, 64, and 66, respectively, and the output signals may be acquired by or provided to a processor (not shown in FIG. 3), which may be configured to detect defects on specimen 60 using the output signals. The processor may detect the defects using the output signals and any suitable method and/or algorithm known in the art. The processor may be further configured as described herein.

The detection subsystem of the inspection system shown in FIG. 3, therefore, includes collectors 62, 64, and 66 and detectors 72, 74, and 76. The detection subsystem shown in FIG. 3 may, however, include any other components of any other detection subsystem(s) described herein. In addition, although the detection subsystem shown in FIG. 3 includes three collectors and three corresponding detectors, it is to be understood that the detection subsystem may include any suitable number of collectors and corresponding detectors. The number of collectors and the number of detectors included in the detection subsystem may or may not be equal.

In one embodiment, a configuration determined according to embodiments described herein for the detection subsystem shown in FIG. 3 includes position(s) of detector 72, detector 74, detector 76, or some combination thereof. For instance, the configuration may include a range of polar angles and a range of azimuthal angles that define the 2D space within the scattering hemisphere in which one or more of the detectors detect light. The range of azimuthal angles may be constant in this embodiment such that the detection subsystem maintains its symmetry about the plane of incidence. Therefore, determining the configuration may, in this embodiment, include determining the range of polar angles for each, some, or one of detectors 72, 74, and 76 that defines the detection space for the detector(s) in the scattering hemisphere. The position(s) of one or more of the collectors may also be determined as described above or may be determined based on the determined configurations of their corresponding detectors. The inspection system shown in FIG. 3 may be further configured as described herein.

Figure 4:
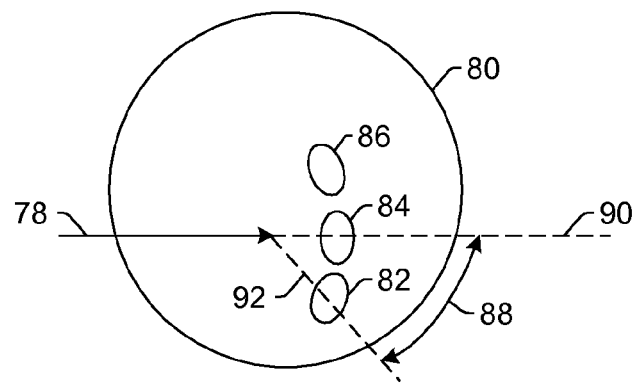

Another embodiment of a light scattering inspection system that includes a detection subsystem for which a configuration may be determined according to embodiments described herein is shown in FIG. 4. In this embodiment, the inspection system includes a light source (not shown). The light source may include any suitable light source known in the art. The light source may be coupled to one or more optical components (not shown) such that the combination of the light source and the optical component(s) directs light 78 to specimen 80 at an oblique angle of incidence. The optical component(s) may include any suitable optical components known in the art such as those described above. Light 78 may be directed to specimen 80 at any suitable oblique angle of incidence.

The inspection system also includes a detection subsystem that includes collectors 82, 84, and 86. Collectors 82, 84, and 86 may be refractive optical elements. In alternative embodiments, each of the collectors may include one or more refractive optical elements and/or one or more reflective optical elements. Collectors 82, 84, and 86 are configured to collect light scattered from the specimen over different ranges of azimuthal angles and different ranges of polar angles. The polar angles may be defined as described above. The azimuthal angle of collector 82 can be defined as angle 88 measured from plane of incidence 90 to axis 92 of collector 82. The range of azimuthal angles across which collector 82 collects light may be defined by angle 88 and characteristics of collector 82. The azimuthal angles of the other collectors and the range of azimuthal angles across which the other collectors collect light may be defined in a similar manner. Therefore, collectors 82, 84, and 86 collect light scattered from the specimen across different 2D spaces within the scattering hemisphere.

The detection subsystem also includes detectors (not shown in FIG. 4), each of which is configured to detect the light collected by one of collectors 82, 84, and 86. The detectors may include any suitable detectors known in the art. The detectors are configured to generate output signals responsive to the light collected by the collectors, and the output signals may be acquired by or provided to a processor (not shown in FIG. 4), which may be configured as described further herein.

The detection subsystem shown in FIG. 4, therefore, includes collectors 82, 84, and 86 and corresponding detectors. The detection subsystem shown in FIG. 4 may, however, include any other components of any other detection subsystem(s) described herein. In addition, although the detection subsystem shown in FIG. 4 includes three collectors, it is to be understood that the detection subsystem may include any suitable number of collectors and corresponding detectors. The number of collectors and the number of detectors included in the detection subsystem may or may not be equal.

In one embodiment, a configuration determined according to embodiments described herein for the detection subsystem shown in FIG. 4 includes position(s) of one or more of the detectors. For instance, the configuration may include a range of polar angles and a range of azimuthal angles that define the 2D space within the scattering hemisphere in which one or more of the detectors detect light. Therefore, determining the configuration may, in this embodiment, include determining the range of polar angles and the range of azimuthal angles for each, some, or one of the detectors that define the detection space for the detector(s) in the scattering hemisphere. The position(s) of one or more of the collectors may also be determined as described above or may be determined based on the determined configurations of their corresponding detectors. The inspection system shown in FIG. 4 may be further configured as described herein.

Figure 5:
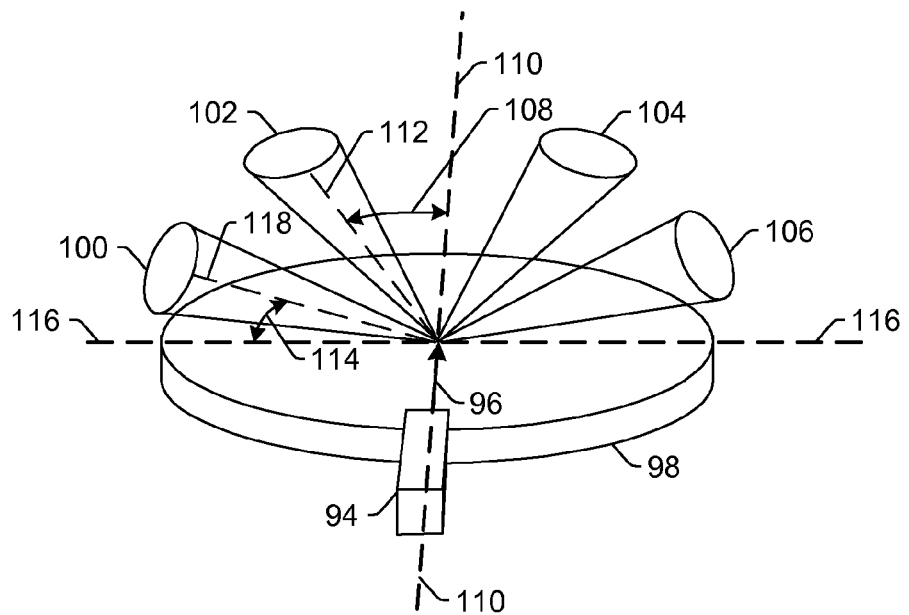

An additional embodiment of a light scattering inspection system that includes a detection subsystem for which a configuration may be determined according to embodiments described herein is shown in FIG. 5. In this embodiment, the inspection system includes light source 94. Light source 94 may include any suitable light source known in the art. Light source 94 may be coupled to optical component(s) (not shown) such that the combination of the light source and the optical component(s) directs light 96 to specimen 98 at an oblique angle of incidence. The optical component(s) may include any suitable optical components known in the art such as those described above. Light 96 may be directed to specimen 98 at any suitable oblique angle of incidence.

The inspection system also includes a detection subsystem that includes collectors 100, 102, 104, and 106. Collectors 100, 102, 104, and 106 may be refractive optical elements. In alternative embodiments, each of the collectors may include one or more refractive optical elements and/or one or more reflective optical elements. Each of the collectors is configured to collect light scattered from the specimen over a different range of azimuthal angles, a different range of polar angles, and a different range of elevation angles. The polar angles may be defined as described above. The azimuthal angle of collector 102 may defined as angle 108 at which light is scattered from the specimen as measured from plane of incidence 110 to axis 112 of collector 102. The range of azimuthal angles across which collector 102 collects light may be defined by angle 108 and characteristics of collector 102. The azimuthal angles of the other collectors and the range of azimuthal angles across which the other collectors collect light may be defined in a similar manner. The elevation angle of collector 100 may be defined as angle 114 from specimen plane 116 to axis 118 of collector 100. The range of elevation angles across which collector 100 collects light may be defined by angle 114 and characteristics of collector 100. The elevation angles of the other collectors and the range of elevation angles across which the other collectors collect light may be defined in a similar manner. Therefore, each of the collectors collects light scattered from the specimen across different 2D spaces within the scattering hemisphere.

The detection subsystem also includes detectors (not shown in FIG. 5), each of which is configured to detect the light collected by one of collectors 100, 102, 104, and 106. The detectors may include any suitable detectors known in the art. The detectors are configured to generate output signals responsive to the light collected by the collectors, and the output signals may be acquired by or provided to a processor (not shown in FIG. 5), which may be configured as described further herein.

The detection subsystem shown in FIG. 5, therefore, includes collectors 100, 102, 104, and 106 and corresponding detectors. The detection subsystem shown in FIG. 5 may, however, include any other components of any other detection subsystem(s) described herein. In addition, although the detection subsystem shown in FIG. 5 includes four collectors, it is to be understood that the detection subsystem may include any suitable number of collectors and corresponding detectors. The number of collectors and the number of detectors included in the detection subsystem may or may not be equal.

In one embodiment, a configuration determined according to embodiments described herein for the detection subsystem shown in FIG. 5 includes position(s) of one or more of the detectors. For instance, the configuration may include a range of polar angles, a range of azimuthal angles, and a range of elevation angles that define the 2D space within the scattering hemisphere in which one or more of the detectors detect light. Therefore, determining the configuration may, in this embodiment, include determining the range of polar angles, the range of azimuthal angles, and the range of elevation angles for each, some, or one of the detectors that define the detection space for the detector(s) in the scattering hemisphere. The position(s) of one or more of the collectors may also be determined as described above or may be determined based on the determined configurations of their corresponding detectors. The inspection system shown in FIG. 5 may be further configured as described herein.

In some embodiments, such as those described above, the detection subsystem includes more than one detector configured to generate signals during inspection of the specimen. In some such embodiments, the configuration determined by the embodiments described herein includes the signals generated by which of the more than one detector that will be used for detection of the potential defect. For example, in one determined configuration, all of the detectors of the detection subsystem may be allowed to generate signals during inspection of the specimen. The configuration may indicate those detectors from which signals will be used for detection of a potential defect. In other words, the signals generated by only some of the detectors (as indicated by the determined configuration) may be used for defect detection. Signals generated by other detectors may essentially be ignored or otherwise not used for defect detection. The signals that are used for defect detection may be determined based on, for example, the S/N values in the 3D map described above at the positions in the 3D map corresponding to the positions of the detectors. In this manner, the signals that are most sensitive or more sensitive to the potential defect may be used for defect detection while the signals that are the least sensitive or less sensitive to the potential defect may be ignored or not used for defect detection.

As described above, in some embodiments, the configuration includes parameter(s) of an aperture plate positioned in the scattering hemisphere. In one such embodiment, the aperture plate includes one or more fixed openings. One embodiment of such an aperture plate is illustrated in FIG. 6. In this embodiment, aperture plate 120 includes openings 122 and 124. Openings 122 and 124 may be fixed in the sense that the positions of the openings within the aperture plate and the dimensions of the openings are fixed. In this manner, parameter(s) of such an aperture plate included in a configuration determined by embodiments described herein may include a position of the aperture plate in the scattering hemisphere. The position of the aperture plate may be determined based on the optimal positions of the openings in the scattering hemisphere. The optimal positions of the openings may be determined from the 3D map as described above.

The position of the aperture plate in the scattering hemisphere may be altered by a device (not shown) coupled to the aperture plate. The device may include, for example, a mechanical device or any other suitable device that can be controlled by, for example, a control subsystem (not shown in FIG. 6), which may be configured as described herein. In this manner, a processor (not shown in FIG. 6), which may be configured as described herein, may provide one or more signals to the control subsystem that are responsive to the determined parameters of aperture plate and that can be used by the control subsystem to change the parameters of the aperture plate via the device. Although aperture plate 120 is shown in FIG. 6 as including two openings having a generally circular shape, it is to be understood that an aperture plate that includes one or more fixed openings may include any suitable number of fixed openings having any suitable shape and dimensions. The fixed opening(s) may be positioned in any suitable arrangement within the aperture plate. Furthermore, the configuration may include parameter(s) for more than one aperture plate positioned in the scattering hemisphere. Each of the aperture plates may be configured similarly or differently.

In another such embodiment, the aperture plate includes one or more adjustable openings. One embodiment of such an aperture plate is shown in FIG. 7. In this embodiment, aperture plate 126 includes opening 128. Opening 128 may be adjustable in the sense that its dimensions may be altered by a device (not shown) coupled to the aperture plate. The device may include, for example, a mechanical device or any other suitable device that can be controlled by, for example, a control subsystem (not shown in FIG. 7) as described herein.

The parameter(s) of the aperture plate that may be included in a configuration determined according to embodiments described herein may include one or more dimensions of opening 128. For example, opening 128 may have radius 130 that is smaller than radius 132 of aperture plate 126 and that can be altered by the device described above. Radius 130 of opening 128 may be altered to change the solid scattering angles of light allowed to pass through the opening. The parameter(s) of aperture plate 126 may also include any other alterable parameters of the aperture plate such as position of the aperture plate in the scattering hemisphere. The parameter(s) of the aperture plate may be determined using the 3D map as described further herein. Although aperture plate 126 is shown in FIG. 7 as including one adjustable opening having a particular shape, it is to be understood that the aperture plate may include any suitable number of adjustable openings having any suitable shape and dimensions, possibly in combination with one or more fixed openings having any suitable shape and dimensions. The fixed and/or adjustable opening(s) may be positioned in any suitable arrangement within the aperture plate.

In another embodiment, the configuration determined according to embodiments described herein includes one or more parameters of a baffle positioned in the scattering hemisphere. One embodiment of a light scattering inspection system that includes a baffle positioned in the scattering hemisphere of the inspection system is shown in FIG. 8. The inspection system shown in FIG. 8 includes light source 134 configured to direct light to optical element 136. Light source 134 may include any suitable light source known in the art. Optical element 136 is configured to direct light to specimen 138 at a substantially normal angle of incidence. However, light source 134 and optical element 136 may alternatively be configured to direct light to specimen 138 at any suitable oblique angle of incidence. Optical element 136 may be a refractive optical element as shown in FIG. 8. Alternatively, optical element 136 may include one or more refractive optical elements and/or one or more reflective optical elements.

Specimen 138 is disposed on stage 140. Stage 140 is configured to support specimen 138 during inspection. Stage 140 may include any suitable mechanical and/or robotic assembly known in the art.

Light scattered from specimen 138 is collected by optical element 142. Optical element 142 may be configured as described above with respect to optical element 136. Optical element 142 may be configured to collect light scattered at any suitable solid scattering angles. In addition, the position of optical element 142 and therefore the angles at which light scattered from specimen 138 is collected by optical element 142 may be determined according to embodiments described herein. Optical element 142 is also configured to direct the collected light through baffle 144 to detector 146. Baffle 144 may have any suitable configuration known in the art. For example, the baffle may include any suitable baffle or field stops known in the art that can be used to block stray photons. Detector 146 may include any suitable detector known in the art.

The detection subsystem shown in FIG. 8, therefore, includes optical element 142, baffle 144, and detector 146. The detection subsystem shown in FIG. 8 may, however, include any other components of any other detection subsystem(s) described herein. In addition, although the detection subsystem shown in FIG. 8 includes one collector, it is to be understood that the detection subsystem may include any suitable number of collectors and corresponding detectors. Some or all of the collectors included in the detection subsystem may be configured to direct light to their corresponding detectors through baffles. In other words, one or more of the detection channels of the inspection system may include baffles.

In one embodiment, a configuration determined according to embodiments described herein for the detection subsystem shown in FIG. 8 includes one or more parameters of baffle 144. For instance, the configuration may include whether or not baffle 144 is positioned in the optical path from optical element 142 to detector 146. The configuration may also or alternatively include one or more dimensions of baffle 144. In addition, the configuration may include any other alterable parameters of the baffle. The inspection system shown in FIG. 8 may be further configured as described herein.

In an additional embodiment, the configuration of the detection subsystem determined according to embodiments described herein includes one or more parameters of a linear polarizing filter positioned in the scattering hemisphere of the inspection system. One embodiment of a light scattering inspection system that includes a filter positioned in the scattering hemisphere of the inspection system is shown in FIG. 9. The embodiment of the system shown in FIG. 9 is similar to that shown in FIG. 8 except that the system shown in FIG. 9 does not include a baffle positioned in the scattering hemisphere and does include a filter positioned in the scattering hemisphere. Elements of FIG. 9 that may be configured similarly to elements shown in FIG. 8 have been indicated with the same reference numerals and therefore will not be described further herein for the sake of brevity.

The detection subsystem shown in FIG. 9 includes filter 148 positioned in the scattering hemisphere of the inspection system. The detection subsystem shown in FIG. 9, therefore, includes optical element 142, filter 148, and detector 146. The detection subsystem shown in FIG. 9 may, however, include any other components of any other detection subsystem(s) described herein. In addition, although the detection subsystem shown in FIG. 9 includes one collector, it is to be understood that the detection subsystem may include any suitable number of collectors and corresponding detectors. Some or all of the collectors included in the detection subsystem may be configured to direct light to their corresponding detectors through filters. In other words, one or more of the detection channels of the inspection system may include filters.

In one embodiment, filter 148 is a linear polarizing filter. In some embodiments, a configuration determined according to embodiments described herein for the detection subsystem shown in FIG. 9 includes one or more parameters of the linear polarizing filter. For instance, the configuration may include whether or not the linear polarizing filter is positioned in the optical path from optical element 142 to detector 146. The configuration may also or alternatively include an arrangement of the linear polarizing filter in the optical path. For example, the arrangement may define the orientation of an axis of the linear polarizing filter in the optical path. In addition, the configuration may include any other alterable parameters of the linear polarizing filter. The inspection system shown in FIG. 9 may be further configured as described herein.

In some embodiments, the linear polarizing filter includes a plurality of linear polarizing segments. Some embodiments of such a linear polarizing filter are described above with respect to FIGS. 1 and 2. Another embodiment of such a linear polarizing filter is shown in FIG. 10. As shown in FIG. 10, linear polarizing filter 150 is a segmented polarizer that is formed of multiple sections 152 of linear polarizers butted against each other, each having a different orientation for pass axis 154. As further shown in FIG. 10, the segmented polarizer may include tens segments, each including a linear polarizer having a differently oriented pass axis. However, it is to be understood that the number of polarizer segments including in linear polarizing filter 150 may vary depending on, for example, the 3D map determined as described above. Linear polarizing filter 150 may be used as filter 148 shown in FIG. 9 or as a filter in any other detection subsystems described herein. The parameter(s) of such a linear polarizing filter that are included in a configuration determined according to embodiments described herein may include, for example, whether or not the linear polarizing filter is positioned in the optical path of the detection subsystem, the orientation of the linear polarizing filter in the optical path of the detection subsystem, and the orientation of the linear polarizing filter with respect to an aperture (not shown in FIG. 10) also included in the detection subsystem.

In another embodiment, the detection subsystem includes an electro-optical light filter positioned in the scattering hemisphere. For example, filter 148 shown in FIG. 9 may be an electro-optical light filter. The electro-optical light filter may include, in one embodiment, a liquid crystal display (LCD)-based electronically controlled light valve. Such a light valve generally includes an array of electrically addressable pixels. The pixels can be turned off or on in any configuration such that individual pixels of the light valve do or do not allow light to pass therethrough. In this manner, the light valve may be used as an adjustable aperture or an adjustable spatial filter.

In another embodiment, the electro-optical light filter may include a micromechanical digital light processor (DLP, which is a registered trademark of Texas Instruments Incorporated, Dallas, Tex.). A micromechanical DLP is another type of electronically controlled light valve that includes an array of tiny mirrors, each of which can be individually tilted. Depending on the position of the micromechanical DLP in the optical path of the detection subsystem, the individual mirrors can be turned "off" or "on" such that some of the mirrors reflect light while other mirrors allow light to pass through the DLP. The micromechanical DLP may include one of the Digital Micromirror Devices (DMD) that are commercially available from Texas Instruments. The electro-optical light filter may also include any other suitable electro-optical light filter known in the art.

In one such embodiment, the configuration determined according to the embodiments described herein includes one or more parameters of the electro-optical light filter. The configuration may include any alterable parameters of the electro-optical light filter (e.g., whether or not the electro-optical light filter is positioned in the optical path of the detection subsystem, which pixels are turned on and which pixels are turned off, which mirrors are turned on and which mirrors are turned off, etc.). The detection subsystem may also include more than one filter, at least one of which is configured as a linear polarizing filter and at least another of which is configured as an electro-optical light filter. In such embodiments, the configuration may include parameter(s) of at least one linear polarizing filter and/or parameter(s) of at least one electro-optical light filter. The linear polarizing filter (s) and the electro-optical light filter(s) may be arranged in the same detection channel or different detection channels.

In some embodiments, the methods described herein include determining a configuration for an additional detection subsystem of the inspection system based on the other portions of the scattering hemisphere such that the additional detection subsystem is sensitive to changes in the specimen and is not sensitive to the potential defect. For example, the portions of the scattering hemisphere that have lower S/N values are not sensitive to the potential defect and may be sensitive to the specimen. These portions of the scattering hemisphere may not be used to determine the configuration of the detection subsystem that will be used to detect the potential defect since these portions of the scattering hemisphere will be more sensitive to the specimen or background noise than the potential defect. However, if the user is interested in information about the specimen, these lower S/N portions may be used to determine a configuration of the detection subsystem that can be used to acquire specimen information. In this manner, the configuration of the additional detection subsystem for specimen information may be the inverse of the optimal configuration for defect detection.

Information about the specimen may be useful in monitoring one or more characteristics of the specimen such as roughness over time. In this manner, the additional detection subsystem may be used to monitor film process quality. For example, the inverse optimal detector may only allow light to pass that is diffusely scattered by a given film in its normal state. Thus, when a shift from the normal state occurs causing a spatial re-distribution of the scattering into solid angles that are not detected for defect detection, the overall average background scattering will decrease. Without the inverse optimal detector, a shift from the normal film state that diffusely scatters more or less light than normal would not produce a detectable change in the output signals of the detection subsystem.

One embodiment of a light scattering inspection system that includes two detection subsystems is shown in FIG. 11. The system of FIG. 11 includes light source 134 and optical element 136, both of which may be configured as described above. Light scattered from specimen 138 disposed upon stage 140, which may be configured as described above, is collected by optical elements 156 and 158. Optical elements 156 and 158 may be configured as described above with respect to optical element 142. Optical elements 156 and 158 are configured to direct the collected light to detectors 160 and 162, respectively. Detectors 160 and 162 may include any suitable detectors known in the art.

As shown in FIG. 11, optical elements 156 and 158 are configured to collect light scattered at different sets of solid angles from specimen 138. For example, optical elements 156 and 158 are configured to collect light scattered from the specimen at different ranges of elevation angles. Optical elements 156 and 158 may also be configured to collect light scattered from the specimen at different ranges of polar angles and/or different ranges of azimuthal angles. Light collected by one of optical elements 156 and 158 may be sensitive to a potential defect (not shown) on the specimen, and light collected by the other optical element may be sensitive to the specimen or a film formed on the specimen. Therefore, output signals generated by one of the detectors may be used to detect potential defects on the specimen, and output signals generated by the other detector may be used to detect changes in the specimen itself or in a film formed on the specimen. In this manner, the configuration determined according to embodiments described herein may include different configurations for different collectors and their corresponding detectors. In other words, the determined configuration may include different configurations for different detection channels of the inspection system.

The configuration may also include parameter(s) for more than one detection channel of an inspection system such that different detection channels are sensitive to different potential defects on the specimen. In such an embodiment, the configuration may include parameter(s) of at least one of the detection channels such that at least one of the detection channels is sensitive to the specimen. For instance, the configuration may include parameter(s) of one detection channel such that the detection channel is sensitive to one type of potential defect, parameter(s) of another detection channel such that this detection channel is sensitive to a different type of potential defect, and parameter(s) of yet another detection channel such that this detection channel is sensitive to the specimen. Furthermore, the inspection system may include two or more detection channels.

In another embodiment, the method is performed for the specimen and a different potential defect to determine an additional configuration for the detection subsystem. In one such embodiment, data acquired by the inspection system during different scans of the specimen with the configuration and the additional configuration can be used to classify defects detected in the data. In this manner, one detection channel of the inspection system can have different configurations during different scans of a specimen. The different configurations may be sensitive to different types of defects. In addition, two or more optimal configurations for different defects types (all on a common specimen type) whose 3D scattering patterns are not alike may be determined. As such, by performing two or more scans of a specimen, each scan performed with the optimal configuration for each defect type, defect intensities at common locations (e.g., x y locations) across the scans may be correlated, and the defects may effectively be classified by type based on the different intensities. In this manner, the configurations may be selected such that differences between the output signals generated by the different configurations during different scans can be used to determine the classification or type of a detected defect.

Figure 12:
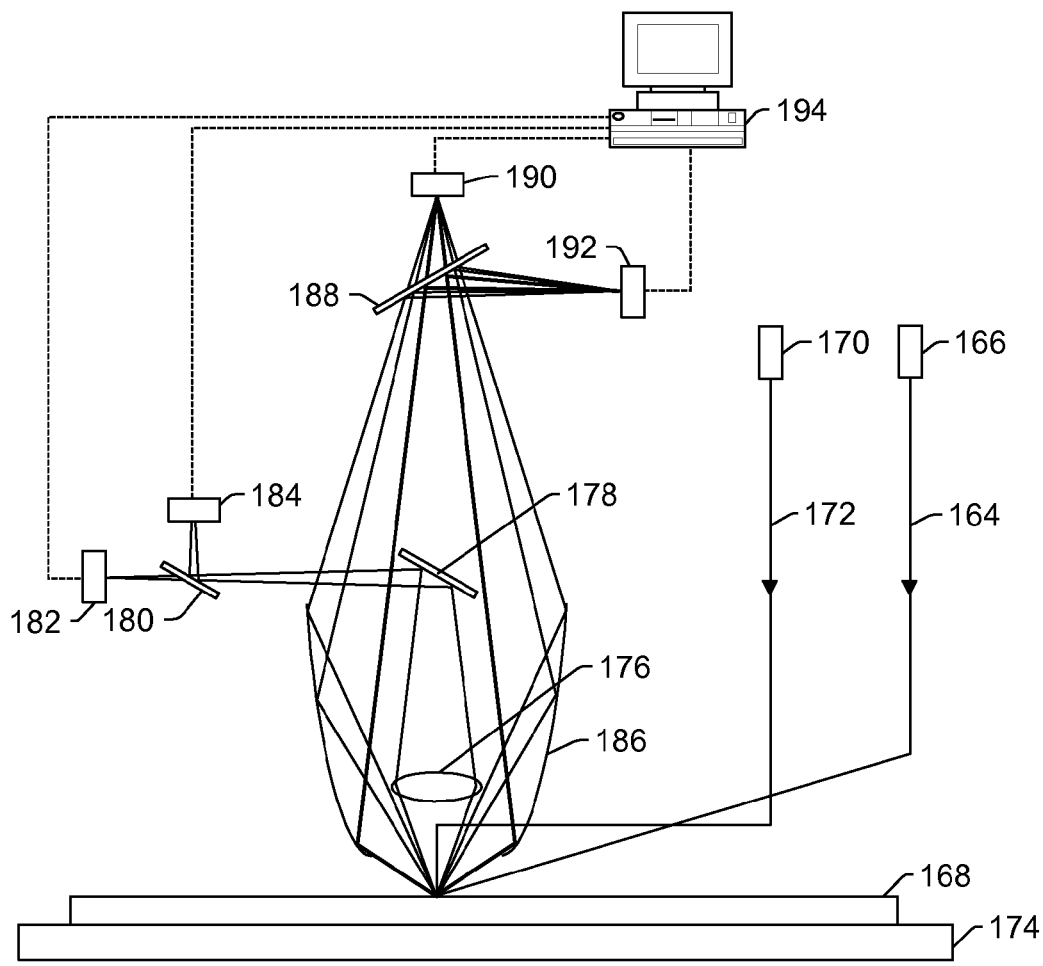

One embodiment of a light scattering inspection system that is configured to inspect a wafer is illustrated in FIG. 12. The system shown in FIG. 12 is configured for unpatterned wafer inspection and is based on the SP1-TBI system, which is commercially available from KLA-Tencor. This inspection system is described in more detail in U.S. Pat. No. 6,538,730 to Vaez-Iravani et al., which is incorporated by reference as if fully set forth herein. The system shown in FIG. 12 may be further configured as described in this patent for patterned and unpatterned wafer inspection. For the sake of clarity, some of the components and details of the system have been omitted from FIG. 12 and the corresponding description presented herein. U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The system shown in FIG. 12 may be further configured as described in these patents.

The system shown in FIG. 12 is configured to direct light to a spot on the wafer and to generate output signals responsive to light scattered from the spot on the wafer. In one embodiment, the system is configured as a laser-based inspection system. In an additional embodiment, the system is configured as a scanning-based inspection system. In addition, the system may be configured as a laser- and scanning-based unpatterned wafer inspection system.

The system includes light source 166, which is configured to generate light 164. The system is configured to direct light 164 to a spot (not shown) on wafer 168 at an oblique angle of incidence. In one embodiment, light 164 directed to the spot on the wafer includes ultraviolet (UV) light. The system may include a number of optical components (not shown) positioned in a path of light 164 such as folding mirror(s), beam splitter(s), polarizing component(s), filter(s), and lenses. The angle of incidence may vary depending on, for example, characteristics of the light, characteristics of the specimen, and characteristics of the defect(s) of interest. One suitable angle of incidence may be about 70° from normal to the upper surface of the wafer.

The system also includes light source 170. Light source 170 is configured to generate light 172, which is directed by the system to the spot on wafer 168 at a substantially normal angle of incidence. In one embodiment, light 172 directed to the spot on the wafer includes UV light. The system may include a number of optical components (not shown) positioned in the path of light 172. These optical components may include any of those described above.

Light sources 166 and 170 may include any suitable light sources known in the art such as lasers. In a different embodiment, the system may include a single light source (not shown) that is used to provide light for both oblique and normal illumination. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The system may include any other suitable combination of a single light source and beam multiplier(s) known in the art. In any of the above embodiments, light 164 may have one or more characteristics such as wavelength and/or polarization that are different than the characteristics of light 172. Alternatively, light 164 may have substantially the same characteristics as light 172.

Wafer 168 is supported on stage 174, which may be rotated and translated such that light 164 and 172 illuminates an area or spot that moves on the wafer in a spiral path. Alternatively, light 164 and 172 may be scanned over the wafer in any manner known to those skilled in the art to trace the spiral path or another type of scan path across the wafer.

Illumination of the wafer will cause scattering of the light from the wafer. In addition, both oblique incidence light and normal incidence light may be scattered from the wafer. The system is configured to collect light scattered from the wafer and to generate output signals responsive to the scattered light. The output signals can be used to detect defects on the wafer as described further herein.

The system includes lens collector 176, mirror 178, beam splitter 180, and detectors 182 and 184, which form a "narrow" channel of the system. In other words, light scattered from the illuminated spot on the wafer along directions relatively close to normal to the surface of the wafer is collected and focused by lens collector 176. In this manner, lens collector 176 collects light scattered from the wafer at relatively "narrow" scattering angles. Lens collector 176 directs the collected light to mirror 178, which directs the light to beam splitter 180. Beam splitter 180 is configured to direct one portion of the light to detector 182 and the other portion of the light to detector 184. One detector may be used to detect light scattered at relatively narrow angles due to illumination by the normal incidence beam, and the other detector may be used to detect light scattered at relatively narrow angles due to illumination by the oblique incidence beam. Detectors 182 and 184 may include any suitable detectors known in the art (e.g., photomultiplier tubes (PMTs)). In addition, detectors 182 and 184 may be similarly or differently configured. The narrow channel portion may include any other optical components (not shown) known in the art. For example, one or more polarizing components may be placed in the path of the collected light. In addition, a spatial filter may be included in the narrow channel to prevent the specular reflection of the normal incidence beam from reaching detectors 182 and 184.

The system also includes ellipsoidal mirror 186, beam splitter 188, and detectors 190 and 192, which form a "wide channel" of the system. In other words, light scattered from the illuminated spot on the wafer along directions relatively far from normal to the surface of the wafer is collected and focused by ellipsoidal mirror 186. In this manner, ellipsoidal mirror 186 collects light scattered from the wafer at relatively "wide" scattering angles. Ellipsoidal mirror 186 directs the collected light to beam splitter 188. Beam splitter 188 is configured to direct one portion of the light to detector 190 and the other portion of the light to detector 192. One detector may be used to detect light scattered at relatively wide angles due to illumination by the normal incidence beam, and the other detector may be used to detect light scattered at relatively wide angles due to illumination by the oblique incidence beam. Detectors 190 and 192 may include any suitable detectors known in the art (e.g., PMTs). In addition, detectors 190 and 192 may be similarly or differently configured. The wide channel may include any other optical components (not shown) known in the art. For example, one or more polarizing components may be placed in the path of the collected light.

As described above, therefore, the inspection system shown in FIG. 12 includes two different detection channels, the narrow channel and the wide channel. The computer-implemented methods described herein can be performed for such an inspection system. For example, the methods may be performed as described above to determine one or more portions of the scattering hemisphere of the inspection system in which the S/N values are higher for data that would be acquired for a specimen and a potential defect on the specimen by the inspection system than in other portions of the scattering hemisphere based on a 3D map determined as described above. The method also includes determining a configuration for the detection subsystem shown in FIG. 12 based on the one or more portions of the scattering hemisphere. The configuration may include parameter(s) of the narrow channel, parameter(s) of the wide channel, or some combination thereof. In addition, the configuration determined for the detection subsystem shown in FIG. 12 may include parameter(s) of any other elements of any other detection subsystem(s) described herein. For example, the configuration may include parameter(s) of one or more linear polarizing filters that are to be positioned in the scattering hemisphere of the system shown in FIG. 12.

Detectors 182, 184, 190, and 192 are configured to generate output signals responsive to the scattered light. Processor 194 is coupled to detectors 182, 184, 190, and 192 by transmission media as shown by the dotted lines in FIG. 12. The transmission media may include any suitable transmission media known in the art. In addition, one or more additional components (not shown) may be interposed between the detectors and the processor such as analog-to-digital converters. In this manner, output signals generated by the detectors can be sent to the processor. The processor is configured to detect defects on the wafer using the output signals. The processor may be configured to use any algorithm or method known in the art for detecting the defects using the output signals. The processor may be further configured as described herein.

The method embodiments described herein may include, in some embodiments, providing signals to a control subsystem (such as that described further herein) of the inspection system that are responsive to the configuration and can be used by the control subsystem to cause the detection subsystem to have the determined configuration. In this manner, the determined optimal configuration may be used to drive computer-controlled devices coupled to the inspection system to realize the optimal configuration in the inspection system hardware. These devices may include, but are not limited to, mechanical aperture stop(s), electro-optical light valve(s), polarizing filter element(s), or some combination thereof, which may be configured as described herein. For example, the optimal configuration may be realized in the physical inspection system by one of several methods, including, but not limited to, adjusting elevations and/or azimuths of detector(s) of an array, turning off or simply ignoring the signals from detector(s) in the array, inserting fixed mechanical aperture(s) into the optics train of detector(s), manipulating a system of one or more baffles in the collection optics train of detector(s), using LCD "light valve" devices in the collection optics train of detector(s), inserting one or more polarization filters, or some combination thereof. In all of the above realizations, insertion of a fixed aperture or adjustment of multiple mechanical components (detectors in an array, multiple baffles, etc.) can be accomplished via computer controlled electronic motors. In addition, computer/electronic control of detector selection, the opaque pixels of an LCD light valve, or a micromechanical DLP, and similar devices is easily amenable to computer control using any method known in the art.

As described above, the method may include determining a configuration of the inspection system for a particular specimen and a potential defect on the specimen. In some embodiments, when a specimen is placed into the inspection system, the method may include determining an identity of the specimen (e.g., by detecting one or more identification marks on the specimen using a device such as bar code reader). The identity of the specimen may then be used by the inspection system or a processor coupled thereto to determine the appropriate configuration for inspection of the specimen. The method may then provide the signals described above to the control subsystem such that the control subsystem causes the detection subsystem to have the appropriate configuration. After the control subsystem alters the configuration of the detection subsystem, the method includes inspecting the specimen.

In this manner, the method may include altering the configuration of the detection subsystem on-the-fly or in real-time. In addition, the method may include altering the configuration of the detection subsystem before inspection of each specimen or determining if the configuration should be altered before inspection of each specimen. In this manner, the method may include determining and possibly altering the configuration of the inspection system on a wafer-to-wafer basis. In another embodiment, the method may include altering the configuration of the detection subsystem between different scans of the specimen. The configurations for the different scans of the specimen may be determined as described above.

Figure 13:
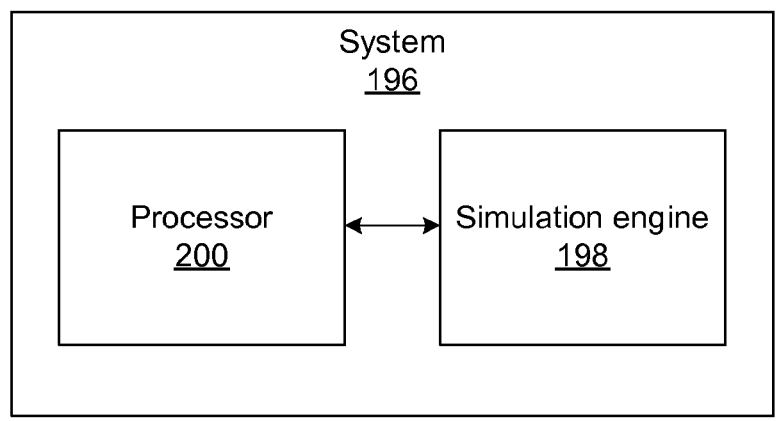
FIG. 13 is a block diagram illustrating one embodiment of a system configured to determine a configuration for a light scattering inspection system.

Another embodiment relates to a system configured to determine a configuration for a light scattering inspection system. One embodiment of such a system is illustrated in FIG. 13. In particular, system 196 is configured to determine a configuration for a light scattering inspection system (not shown in FIG. 13). The inspection system may be configured as described herein. System 196 does not include the inspection system, but may be coupled to the inspection system (e.g., via a transmission medium or a data link) such that system 196 can provide the configuration to the inspection system.

The system includes simulation engine 198. Simulation engine 198 is configured to determine a 3D map of S/N values of data that would be acquired for a specimen and a potential defect on the specimen by the inspection system. Simulation engine 198 may be configured to determine the 3D map according to any of the embodiments described herein. Simulation engine 198 may be further configured as described herein. In addition, simulation engine 198 may include any appropriate hardware and/or software that can be configured as described herein.

System 196 also includes processor 200. Processor 200 is configured to determine one or more portions of the scattering hemisphere in which the S/N values are higher than in other portions of the scattering hemisphere based on the 3D map determined by simulation engine 198. Therefore, processor 200 may be coupled to simulation engine 198 (e.g., via a transmission medium or data link) such that processor 200 can receive the 3D map from the simulation engine. Although processor 200 and simulation engine 198 may appear to be physically located in proximity to each other within system 196 in FIG. 13, it is to be understood that the processor and the simulation engine may be housed physically separately and possibly in remote locations. In such instances, the processor and the simulation engine may be coupled by a transmission medium that includes "wired" and/or "wireless" portions. The transmission medium may include any suitable transmission medium known in the art.

Processor 200 may be configured to determine the one or more portions of the scattering hemisphere according to any of the embodiments described herein. Processor 200 is also configured to determine a configuration for a detection subsystem of the inspection system based on the one or more portions of the scattering hemisphere. The processor may be configured to determine the configuration according to any of the embodiments described herein. The processor may be configured to perform any other step(s) of any other embodiments described herein.

Processor 200 may take various forms, including a personal computer system, mainframe computer system, workstation, image computer, parallel processor, or any other device known in the art. In general, the term "computer system" may be broadly defined to encompass any device having one or more processors, which executes instructions from a memory medium. The system may be further configured as described herein. In addition, the system has all of the advantages of the method embodiments described herein.

Program instructions executable on a processor (e.g., processor 200) or computer system for performing a method such as those described herein may be transmitted over or stored on a carrier medium. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Figure 14:
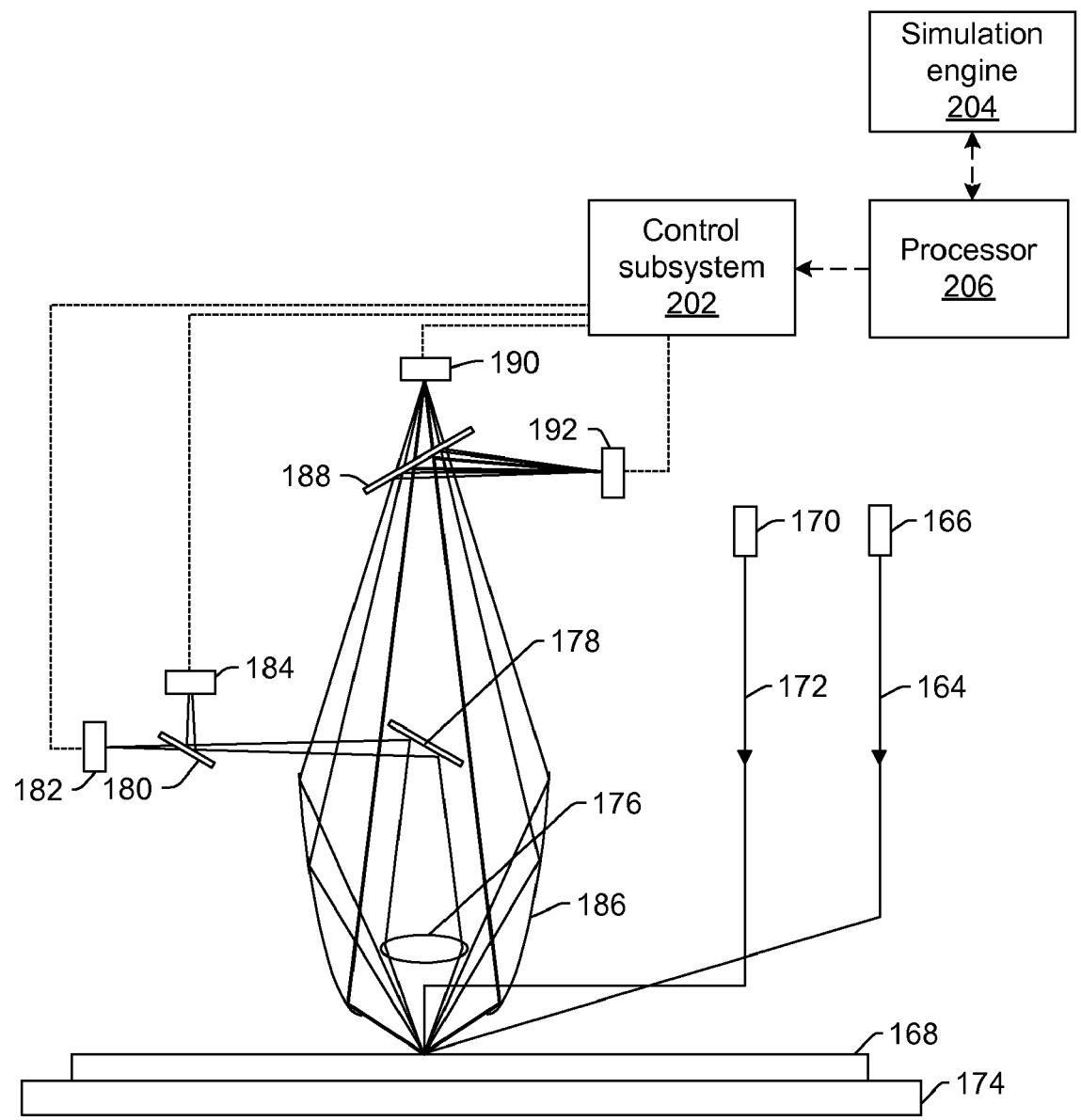
FIG. 14 is a schematic diagram illustrating one embodiment of a system configured to determine an inspection system configuration for a specimen.

An additional embodiment relates to a system configured to determine an inspection system configuration for a specimen. One embodiment of such a system is shown in FIG. 14. The system shown in FIG. 14 includes the inspection system shown in FIG. 12. Therefore, the inspection system shown in FIG. 14 will not be described further herein for the sake of brevity. However, the system shown in FIG. 14 may include any other inspection system described herein. In this embodiment, the inspection system includes control subsystem 202 that is configured to alter one or more parameters of a detection subsystem of the inspection system. For example, as shown by the dotted lines in FIG. 14, control subsystem 202 may be coupled to detectors 182, 184, 190, and 192. Control subsystem 202 may be coupled to the detectors such that the control subsystem can alter one or more parameters of the detectors. Control subsystem 202 may be coupled to other elements of the detection subsystem or other devices (e.g., mechanical devices) coupled to elements of the detection subsystem in a similar manner. Control subsystem 202 may include any suitable device known in the art.

The system shown in FIG. 14 also includes simulation engine 204. The simulation engine is configured to determine a 3D map of S/N values of data that would be acquired for the specimen and a potential defect on the specimen by the inspection system. The simulation engine may be configured to determine the 3D map according to any of the embodiments described herein. For instance, in one embodiment, the simulation engine is configured to determine the 3D map based on information about the specimen acquired by a metrology system (not shown). The metrology system is not included in the system embodiment shown in FIG. 14. Instead, the system may acquire the information from the metrology system (e.g., via a data link or transmission medium) or from a database (e.g., a fab database) to which both the system and the metrology system are coupled. The information about the specimen may be information about the roughness of the specimen. In such an example, the metrology system may be an AFM system or any other appropriate metrology system known in the art. In another embodiment, the simulation engine is configured to determine the 3D map for different specimens based on information about the different specimens. Simulation engine 204 may be further configured as described above with respect to simulation engine 198.

The system shown in FIG. 14 further includes processor 206. Processor 206 is configured to determine one or more portions of the scattering hemisphere in which the S/N values are higher than in other portions of the scattering hemisphere based on the 3D map generated by simulation engine 204. Processor 206 is also configured to determine a configuration for the detection subsystem based on the one or more portions of the scattering hemisphere. The processor may be configured to perform these steps according to any of the embodiments described herein.

The processor is further configured to provide signals to the control subsystem that are responsive to the configuration and can be used by the control subsystem to cause the detection subsystem to have the determined configuration. For example, the processor may be coupled to control subsystem 202 by a transmission medium that may include wired and/or wireless portions. In this manner, the processor may send the signals to the control subsystem via the transmission medium. The transmission medium may include any suitable transmission medium known in the art. The control subsystem can use the signals to cause the detection subsystem to have the determined configuration as described above.

In some embodiments, the processor is configured to determine the configuration for the detection subsystem for different specimens and to provide different signals to the control subsystem in real time based on the specimen being inspected by the inspection system. The different signals are responsive to the configurations and can be used by the control subsystem to cause the detection subsystem to have one of the determined configurations. In one such embodiment, when a specimen is placed into the inspection system, the processor determines an identity of the specimen (e.g., using output signals responsive to one or more identification marks on the specimen generated by a device such as bar code reader). The identity of the specimen may be used by the processor to determine the appropriate configuration for inspection of the specimen. The processor may provide signals responsive to the appropriate configuration to the control subsystem such that the control subsystem causes the detection subsystem to have the appropriate configuration. After the control subsystem alters the configuration of the detection subsystem, the specimen is inspected by the inspection system.

In this manner, the processor via the control subsystem may alter the configuration of the detection subsystem on-the-fly or in real-time. In addition, the processor via the control subsystem may alter the configuration of the detection subsystem before inspection of each specimen or to determine if the configuration should be altered before inspection of each specimen. In this manner, the processor may determine and possibly alter the configuration of the inspection system on a wafer-to-wafer basis. In another embodiment, the processor may be configured to alter the configuration of the detection subsystem between different scans of the specimen. The configurations for the different scans of the specimen may be determined as described above.

Further modifications and alternative embodiments of various aspects of the invention may be apparent to those skilled in the art in view of this description. For example, computer-implemented methods and systems for determining a configuration for a light scattering inspection system are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for determining a configuration for a light scattering inspection system, comprising:
    determining a three-dimensional map of signal-to-noise ratio values for data that would be acquired for a specimen and a potential defect on the specimen by the light scattering inspection system across a scattering hemisphere of the inspection system;
    determining one or more portions of the scattering hemisphere in which the signal-to-noise ratio values are higher than in other portions of the scattering hemisphere based on the three-dimensional map; and
    determining a configuration for a detection subsystem of the inspection system based on the one or more portions of the scattering hemisphere.

2. The method of claim 1, wherein the scattering hemisphere comprises an entire scattering hemisphere of the inspection system.

3. The method of claim 1, wherein said determining the three-dimensional map comprises determining different three-dimensional distributions of light that would be diffusely reflected from the specimen and the potential defect when illuminated by the inspection system and determining the three-dimensional map from the different three-dimensional distributions.

4. The method of claim 1, wherein said determining the three-dimensional map comprises determining a three-dimensional distribution of light that would be diffusely reflected from the specimen when illuminated by the inspection system based on a power spectral density function determined from metrology data for the specimen.

5. The method of claim 1, wherein said determining the three-dimensional map comprises determining a three-dimensional distribution of light that would be diffusely reflected from the specimen when illuminated by the inspection system based on a power spectral density function determined from metrology data for the specimen and information about one or more films that will be present on the specimen and are at least partially transparent to illumination by the inspection system.

6. The method of claim 1, wherein said determining the three-dimensional map comprises determining a three-dimensional distribution of light that would be diffusely reflected from the potential defect based on optical constants of the potential defect and complex indices of the specimen.

7. The method of claim 1, further comprising prior to said determining the one or more portions of the scattering hemisphere, removing one or more portions of the three-dimensional map based on areas of the scattering hemisphere in which the inspection system cannot collect light.

8. The method of claim 1, wherein the configuration comprises positions of one or more detectors in the scattering hemisphere.

9. The method of claim 1, wherein the detection subsystem comprises more than one detector configured to generate signals during inspection of the specimen, and wherein the configuration comprises the signals generated by which of the more than one detector that will be used for detection of the potential defect.

10. The method of claim 1, wherein the configuration comprises one or more parameters of an aperture plate positioned in the scattering hemisphere, and wherein the aperture plate comprises one or more fixed openings.

11. The method of claim 1, wherein the configuration comprises one or more parameters of an aperture plate positioned in the scattering hemisphere, and wherein the aperture plate comprises one or more adjustable openings.

12. The method of claim 1, wherein the configuration comprises one or more parameters of a baffle positioned in the scattering hemisphere.

13. The method of claim 1, wherein the configuration comprises one or more parameters of a linear polarizing filter positioned in the scattering hemisphere.

14. The method of claim 1, wherein the configuration comprises one or more parameters of a linear polarizing filter positioned in the scattering hemisphere, and wherein the linear polarizing filter comprises a plurality of linear polarizing segments.

15. The method of claim 1, wherein the configuration comprises one or more parameters of an electro-optical light filter positioned in the scattering hemisphere.

16. The method of claim 1, further comprising providing signals to a control subsystem of the inspection system that are responsive to the configuration and can be used by the control subsystem to cause the detection subsystem to have the determined configuration.

17. The method of claim 1, further comprising determining a configuration for an additional detection subsystem of the inspection system based on the other portions of the scattering hemisphere such that the additional detection subsystem in the determined configuration is sensitive to changes in the specimen and is not sensitive to the potential defect.

18. The method of claim 1, further comprising performing the method for the specimen and a different potential defect to determine an additional configuration for the detection subsystem, wherein data acquired by the inspection system during different scans of the specimen with the configuration and the additional configuration can be used to classify defects detected in the data.

19. A system configured to determine a configuration for a light scattering inspection system, comprising:

a simulation engine configured to determine a three-dimensional map of signal-to-noise ratio values of data that would be acquired for a specimen and a potential defect on the specimen by the light scattering inspection system across a scattering hemisphere of the inspection system; and a processor configured to determine one or more portions of the scattering hemisphere in which the signal-to-noise ratio values are higher than in other portions of the scattering hemisphere based on the three-dimensional map and to determine a configuration for a detection subsystem of the inspection system based on the one or more portions of the scattering hemisphere.

20. A system configured to determine an inspection system configuration for a specimen, comprising:

a light scattering inspection system comprising a control subsystem configured to alter one or more parameters of a detection subsystem of the inspection system;

a simulation engine configured to determine a three-dimensional map of signal-to-noise ratio values of data that would be acquired for the specimen and a potential defect on the specimen by the light scattering inspection system across a scattering hemisphere of the inspection system; and a processor configured to determine one or more portions of the scattering hemisphere in which the signal-to-noise ratio values are higher than in other portions of the scattering hemisphere based on the three-dimensional map, to determine a configuration for the detection subsystem based on the one or more portions of the scattering hemisphere, and to provide signals to the control subsystem that are responsive to the configuration and can be used by the control subsystem to cause the detection subsystem to have the determined configuration.

21. The system of claim 20, wherein the simulation engine is further configured to determine the three-dimensional map based on information about the specimen acquired by a metrology system.

22. The system of claim 20, wherein the simulation engine is further configured to determine the three-dimensional map for different specimens based on information about the different specimens, wherein the processor is further configured to determine the configuration for the detection subsystem for the different specimens and to provide different signals to the control subsystem of the inspection system in real time based on the specimen being inspected by the inspection system, and wherein the different signals are responsive to the configurations and can be used by the control subsystem to cause the detection subsystem to have one of the determined configurations.

* * * * *